(12) United States Patent
Wang (10) Patent No.: US 9,041,785 B2
(45) Date of Patent: *May 26, 2015

(54) MULTIPLE CAPSULE CAMERA APPARATUS AND METHODS FOR USING THE SAME

(75) Inventor: Kang-Huai Wang, Saratoga, CA (US)

(73) Assignee: Capso Vision Inc, Saratoga, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 13/609,253

(22) Filed: Sep. 11, 2012

(65) Prior Publication Data

US 2013/0242070 A1 Sep. 19, 2013

Related U.S. Application Data

(63) Continuation of application No. 12/430,072, filed on Apr. 25, 2009, now Pat. No. 8,300,091.

(51) Int. Cl.
*A61B 1/00* (2006.01)
*A61B 1/04* (2006.01)
*H04N 7/18* (2006.01)
*A61B 1/06* (2006.01)

(52) U.S. Cl.
CPC ......... *A61B 1/00029* (2013.01); *A61B 1/00016* (2013.01); *A61B 1/0002* (2013.01); *A61B 1/00032* (2013.01); *A61B 1/00036* (2013.01); *A61B 1/041* (2013.01); *A61B 1/0684* (2013.01); *A61B 2560/0209* (2013.01); *H04N 7/185* (2013.01)

(58) Field of Classification Search
CPC .. H04N 7/185; A61B 1/00016; A61B 1/0002; A61B 1/00032; A61B 1/00036; A61B 1/041; A61B 1/0684; A61B 2560/0209
See application file for complete search history.

(56) References Cited

U.S. PATENT DOCUMENTS

| 4,278,077 | A | 7/1981 | Mizumoto |
| 5,604,531 | A | 2/1997 | Iddan et al. |
| 6,428,469 | B1 | 8/2002 | Iddan et al. |
| 6,709,387 | B1 | 3/2004 | Glukhovsky et al. |
| 6,939,292 | B2 | 9/2005 | Mizumoto |
| 7,495,993 | B2 | 2/2009 | Wang |
| 8,300,091 | B2 * | 10/2012 | Wang .............................. 348/65 |
| 2006/0031378 | A1 | 2/2006 | Vallapureddy et al. |
| 2007/0066868 | A1 | 3/2007 | Shikii |
| 2008/0269664 | A1 | 10/2008 | Trovato et al. |

* cited by examiner

*Primary Examiner* — Patrice Winder
(74) *Attorney, Agent, or Firm* — Blairtech Solution LLC (57) ABSTRACT

A multiple capsule camera apparatus is disclosed to enhance the rate of detection and/or extend the overall imaging period. The multiple capsule camera apparatus coordinates the operations of the camera according to a schedule so that one camera may enter an active mode when the other camera is anticipated to have a low battery level. The capsule cameras may also coordinate their operations by communication with each other through a wireless link. A base station may also be used to coordinate the capsule camera operations with a wireless link established between the base station and each capsule camera.

8 Claims, 8 Drawing Sheets

MULTIPLE CAPSULE CAMERA APPARATUS AND METHODS FOR USING THE SAME

CROSS REFERENCE TO RELATED APPLICATIONS

The present invention is a continuation of and claims priority to U.S. Non-Provisional patent application, Ser. No. 12/430,072, filed on Apr. 25, 2009, entitled "MULTIPLE CAPSULE CAMERA APPARATUS AND METHODS FOR USING THE SAME". The U.S. Non-Provisional patent application is hereby incorporated by reference in its entirety.

FIELD OF THE INVENTION

The present invention relates to diagnostic imaging inside the human body. In particular, the present invention relates to utilizing multiple capsule cameras.

DISCUSSION OF THE RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An early example of a camera in a swallowable capsule is described in U.S. Pat. No. 5,604,531. Other patents, such as U.S. Pat. Nos. 6,709,387 and 6,428,469, describe more details of such a system, using a transmitter to send the camera images to an external receiver. Still other patents, including U.S. Pat. 4,278,077, describe similar technologies. For example, U.S. Pat. No. 4,278,077 shows a capsule with a camera for the stomach, which includes film in the camera. U.S. Pat. No. 6,939,292 shows a capsule with a buffering memory, a timer, and a transmitter.

One advantage of an autonomous encapsulated camera with an internal battery is that measurements may be made with the patient ambulatory, out of the hospital, and with moderate restriction of activity. The base station includes an antenna array surrounding the bodily region of interest and this array can be temporarily affixed to the skin or incorporated into a wearable vest. A data recorder is attached to a belt and includes a battery power supply and a data storage medium for saving recorded images and other data for subsequent uploading onto a diagnostic computer system.

A typical procedure consists of an inpatient visit in the morning during which a clinician attaches the base station apparatus to the patient and the patient swallows the capsule. The system records images beginning just prior to swallowing and records images of the gastrointestinal (GI) tract until its battery becomes fully discharged. Peristalsis propels the capsule through the GI tract. The rate of passage depends on the degree of motility. Usually, the small intestine is traversed in 4 to 8 hours. After a prescribed period, the patient returns the data recorder to the clinician who then uploads the data onto a computer for subsequent viewing and analysis. The capsule is passed in time through the rectum and need not be retrieved.

There is also another type of autonomous capsule camera that utilizes on-board data recorder to store captured image data from the camera and other associated data. Therefore such capsule camera does not require a built-in radio transmitter to send data for the captured images. U.S. Pat. No. 6,800,060 describes a swallowable data-recorder capsule that may be retrieved after passing from the body. However, this system specifies an expensive and rare ultra-high-density atomic-resolution storage (ARS) medium. U.S. Pat. No. 7,495,993 describes a semiconductor memory as on-board storage for capsule camera applications. This semiconductor based on-board storage offers several advantages over the ARS storage in terms of lower cost and flexible data access.

The capsule camera allows the GI tract from the esophagus down to the end of the small intestine, especially the small intestine, to be imaged in its entirety, although it is not optimized to detect anomalies in the stomach. Color photographic images are captured so that anomalies can be detected even when only small visually recognizable characteristics, not topography, are available. The procedure is pain-free and requires no anesthesia. Risks associated with the capsule passing through the body are minimal—certainly, the risk of perforation is much reduced relative to endoscopy. The cost of the procedure is also less than for an endoscopy due to the decreased use of clinician time and clinic facilities, and the absence of anesthesia.

A limitation of the current solutions is their inability to reliably image the colon. The colon presents a number of challenges for the imaging system. A number of complications arise because the capsule takes longer to pass through the entire GI tract than just through the small intestine. In fact, ingested material can easily take 24 hours or longer to pass through the colon, although this time can be reduced with motility-enhancing drugs. Therefore to use the capsule camera for imaging the GI tract through colon would thus require extended battery life.

While the technology of capsule camera has advanced over the years, the detection rate of anomalies by a commercially available capsule camera is around 80% as reported in a recent study. Accordingly, it is desirable to further improve the detection rate. On the other hand, the passage rate for a swallowable camera is about 4 to 8 hours in the small intestines and it may take 24 hours or longer for the camera to go through the colon. Therefore, it is desirable to provide a capsule camera apparatus with extended imaging time so that it may reliably be used for imaging the GI tract through colon. This need is the same for the type of autonomous capsule camera using radio transmitter to send the captured images, as well as the type of autonomous capsule camera using onboard memory for images recorded by the digital camera.

BRIEF SUMMARY

The present invention provides an apparatus and method for improving reliability of capsule camera by utilizing multiple capsule cameras to increase the detection rate for anomalies. According to one embodiment of the present invention, a cooperative multiple capsule camera apparatus and a method provide a plurality of capsule cameras, wherein the capsule camera includes a control module to control capsule camera operations according to a schedule.

According to one embodiment, the control module includes a timer to track elapse time since the capsule camera is activated and the camera operations include a sleep mode and an active mode. The capsule camera may initially start in the sleep mode and the operation mode is determined by the control module according to a schedule including a list of the pre-defined values, which can be stored in a memory space of the control module, corresponding to the elapse times for the respective capsule cameras.

According to one embodiment, a cooperative multiple capsule camera apparatus and a method provide a first capsule camera and a second capsule camera, wherein each of the capsule cameras includes a battery, an image sensor, illuminating LEDs, and a control module. The first capsule cameras further includes a first wireless communication module and the second capsule camera further includes a second wireless communication module. A wireless link between the first wireless communication module and the second wireless communication module is established and the control module controls capsule camera operations using information received from the wireless link.

According to one embodiment, the capsule cameras function in a relay mode so that capsule cameras will be in the active mode by taking turns. According to another embodiment, the first capsule camera sends status information of the first capsule camera to the second capsule camera through the wireless link. Furthermore, the status information may include battery status such as battery voltage level or the energy consumption by the battery, a number of pictures captured by the image sensor, or an electrical current value of the illuminating LEDs.

According to one embodiment, the camera operations include a sleep mode and an active mode, where in the second capsule camera is initially switched from the sleep mode to the active mode using the first capsule camera status information received from the wireless link and also the second capsule camera and the first capsule camera may have a period of time as being both in the active mode.

According to one embodiment, the status information is transmitted periodically, or transmitted as being triggered by low battery status, or by energy consumption profile, or by a low electrical current value of the illuminating LEDs, or by the number of pictures captured by the image sensor.

According to one embodiment, a cooperative multiple capsule camera apparatus and a method provide a plurality of capsule cameras and a base station. The capsule camera includes a battery, an image sensor, illuminating LEDs, a first wireless communication module and a control module. The base station has a second wireless communication module. The base station coordinates with the control module in the capsule camera through a wireless link between the first wireless communication module and the second wireless communication module and the control module controls capsule camera operations using information received from the base station through the wireless link.

According to one embodiment, the information transmitted from the first wireless communication module to the second wireless communication module includes status of the respective capsule camera.

DETAILED DESCRIPTION OF THE INVENTION

As mentioned earlier that a limitation of the current single capsule camera is its inability to reliably image the colon. The colon presents a number of challenges for the imaging system. A number of complications arise because the capsule takes longer to pass through the entire GI tract than just through the small intestine. In fact, ingested material can easily take 24 hours or longer to pass through the colon, though this time can be reduced with motility-enhancing drugs. Imaging the colon with an existing system may face the challenge of long battery life for extended imaging time.

One objective of the present invention is to improve the detection rate of anomalies by using multiple capsule cameras. While the detection rate of using a conventional single capsule camera has been improved over the years, the detection rate of anomalies achieved today is close to 80%. Certainly it is desirable to further improve the detection rate. It is advantageous to have some parts or the complete GI tract imaged by multiple capsule cameras to enhance the rate of detection. The chance that an anomaly is missed by all the capsule cameras is substantially less than that by a single capsule camera. Therefore, it is desirable to have some parts or the complete the GI tracts imaged by multiple capsule cameras where the multiple capsule cameras are coordinated in a cooperative fashion. The capsule cameras may be coordinated to have coverage by multiple cameras in some parts of the GI tract for enhancing rate of detection, and to work in turns in other parts of the GI tract.

Another objective of the present invention is to extend the imaging time period of the GI tracts by using multiple capsule cameras. While the battery life of a typical single capsule camera has been improved over the years, the period for a capsule camera to traverse the entire GI tract may be lengthy. On the other hand, the battery life also depends on the number of pictures being captured as well as the light intensity of the illuminating LEDs. A brighter LED illumination will help to see or capture clearer pictures. However, clearer pictures are obtained at the cost of shorten battery life. In order to see or capture clearer pictures with brighter LED illumination while maintaining adequate battery life, it will be beneficial to use multiple capsule cameras in turns. In the multiple capsule camera system, the cameras may work in a relay mode wherein one camera may enter active mode after the other is anticipated to run out of battery. In the multiple capsule camera system, it is important to coordinate the cameras to operate in a cooperative way so that their operation modes are properly coordinated.

Figure 1:
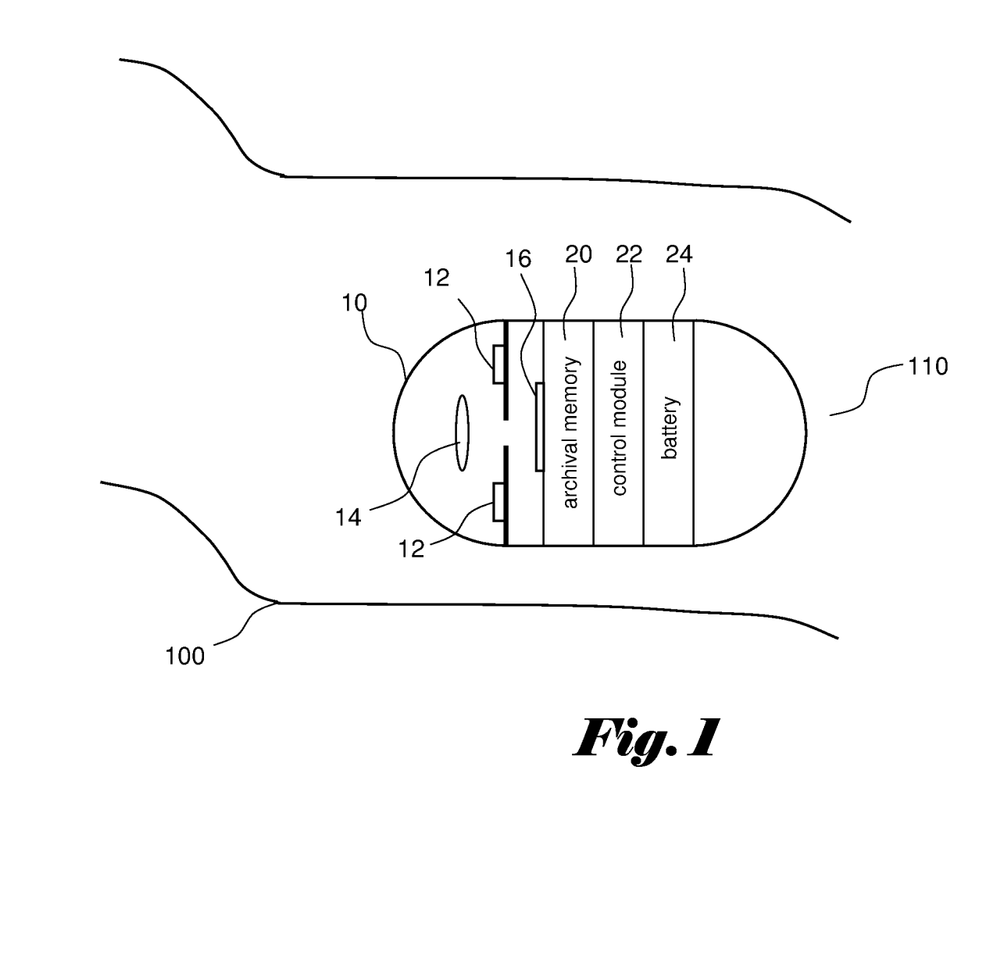
FIG. 1 shows schematically single capsule camera system in the GI tract.

FIG. 1 shows a single swallowable capsule system 110, inside body lumen 100. Lumen 100 may be, for example, the colon, small intestines, the esophagus, or the stomach. Capsule system 110 is an exemplary capsule camera, wherein only the key components relevant to the current invention are illustrated. Capsule system 110 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 00 walls, and to allow the scattered light from the lumen 100 walls to be collected and imaged within the capsule. Capsule housing 10 also protects lumen 100 from direct contact with the foreign material inside capsule housing 10. Capsule housing 10 is provided a shape that enables it to be swallowed easily and later to pass through of the GI tract. Generally, capsule housing 10 is sterile, made of non-toxic material, and is sufficiently smooth to minimize the chance of lodging within the lumen.

As shown in FIG. 1, capsule system 110 includes illuminating system 12 and a camera that includes optical system 14 and image sensor 16. An image captured by image sensor 16 may be stored in a semiconductor nonvolatile archival memory 20 to allow the images to be retrieved at a docking station outside the body, after the capsule is recovered. System 110 includes battery power supply 24. Capsule system 110 may be propelled through the GI tract by peristalsis. In addition to the image sensor 16, other sensors (for example, PH meter and ultrasonic sensor) and other components (for example ultrasonic emitter), not shown, may also be included in the capsule system 110.

Illuminating system 12 may be implemented by LEDs. In FIG. 1, the LEDs are located adjacent to the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation. The control module is also responsible for determining the operating mode of the capsule camera, such as sleep mode or active mode. At sleep mode, the capsule camera system is maintained at a minimum power consumption to conserve battery. Usually a timer is kept alive and a processing device such as a processor, a microcontroller or digital logic of the controller is in an idle state waiting for interrupt. Upon interrupt, the capsule camera system may enter the active mode and began capturing images. In the active mode, the capsule camera system may still have the timer running for further interrupt and entering new operation mode. For example, a new mode may be a sleep mode so that the capsule camera will switch from the active mode to the sleep mode again.

Figure 2:
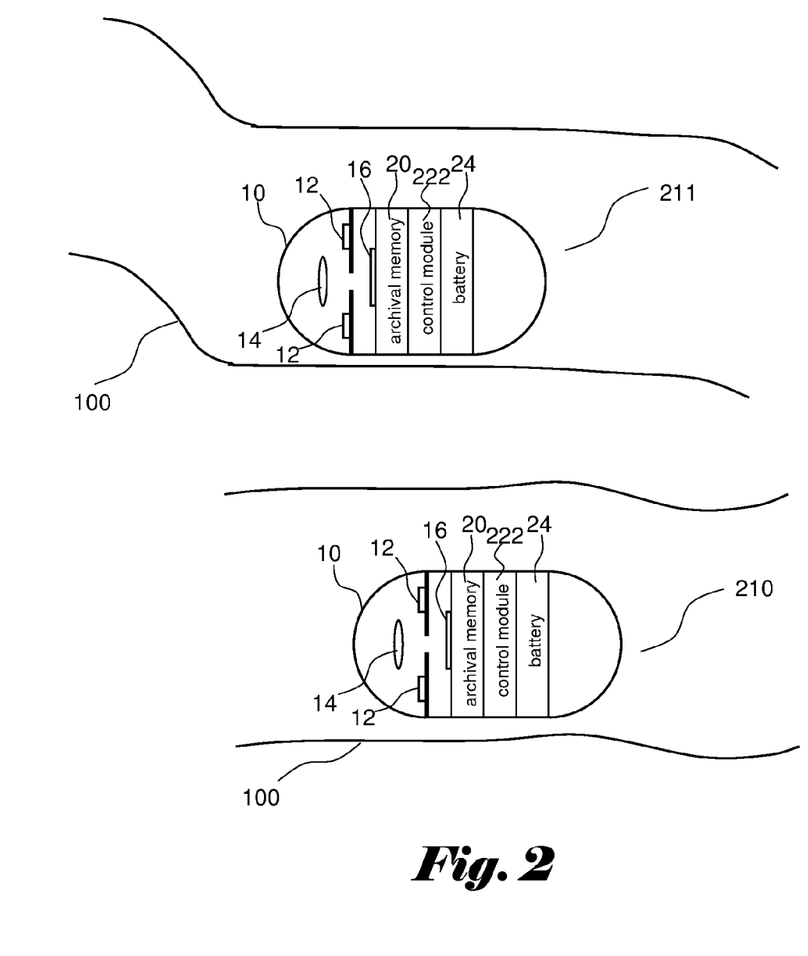
FIG. 2 shows schematically multiple capsule camera system in the GI tract.

FIG. 2 shows an exemplary multiple capsule camera system, wherein two capsule cameras, a first capsule camera 210 and a second capsule camera 211, are used. While two capsule cameras are used in the exemplary multiple camera system, the multiple capsule camera system may use more than two capsule cameras. The first capsule camera 210 and the second capsule camera 211 may be swallowed at the same time or at different times. FIG. 2 illustrates a scenario that the two cameras are at two different sections inside the body lumen 100. Capsule cameras 210 and 211 include a respective control module 222. Each of the control modules contains a respective schedule which is not explicitly shown in the drawing. The schedule data may be stored in the memory, such as EEPROM, flash memory or ROM of the respective control module.

The schedule includes information regarding the operation mode profile along the time. For example, the schedule may be a table containing a list of time instances and corresponding operation mode for each time instance, wherein the time instances may be measured from the point when the camera is activated that often occurs immediate before the capsule camera is swallowed. Since the capsule cameras may be swallowed at different times, the schedule will incorporate the time difference factor into the time table. By properly designing the schedules for the capsule cameras, improved detection rate or extended imaging time may be achieved. For example, two capsule cameras may have identical schedule and are swallowed at the same time, the two cameras will likely image same sections of the body lumen. In other words, a desired section of the body lumen will be imaged by both cameras. Therefore, the chances of missing anomalies will be reduced. In another example, a first capsule camera and a second capsule camera may be swallowed at the same time and the second camera may enter into an active mode at a period of time after the first camera enters an active mode. Therefore, the second camera will likely be still operative when the first camera exhausts its battery. The control modules are responsible to determine the operation mode of the respective capsule camera according to the schedule.

Figure 3:
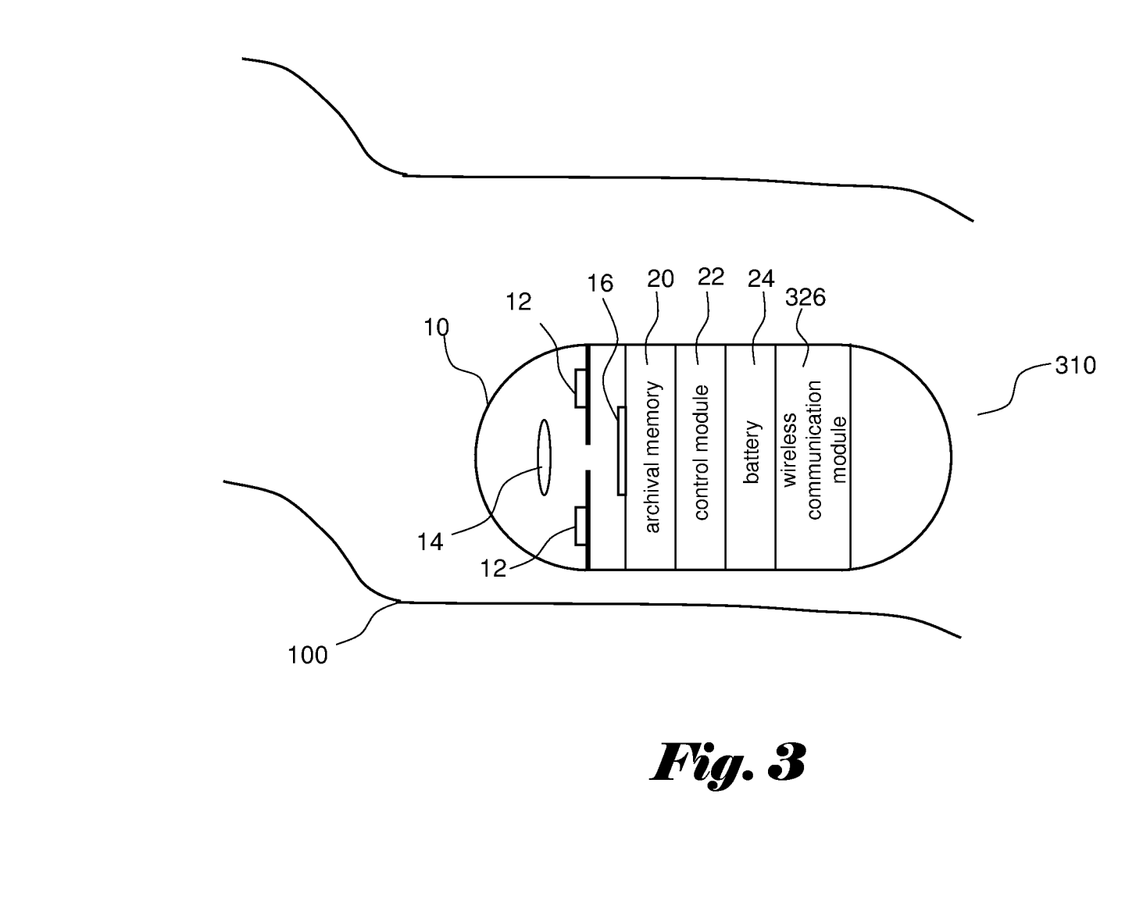
FIG. 3 shows schematically single capsule camera system, having a wireless communication module, in the GI tract.

FIG. 3 shows another single capsule camera 310 inside the body lumen 100. Capsule system 310 is an exemplary capsule camera, wherein only the key components relevant to the current invention are illustrated. The capsule camera system 310 includes a wireless communication module 326, which may be a transmitter, a receiver or a combined device with integrated transmitter/receiver. The wireless transmitter for the digital image data usually is a high-speed data link in order to send out the captured image data in real time. The antenna or antennas for the wireless communication module are not shown. The wireless communication module 326 is used primarily for wireless communication purposes to transmit status information to or receive status information from other capsule cameras. This communication typically is of low data rate in nature and consumes very low power. The capsule camera system 310 may also have a separate wireless communication module for high-speed communication to send pictures capture by the sensor 16 to a receiving device outside the body. This high-speed wireless transmitter and the wireless communication module 326 may be combined into a single device to save cost and space.

Figure 4:
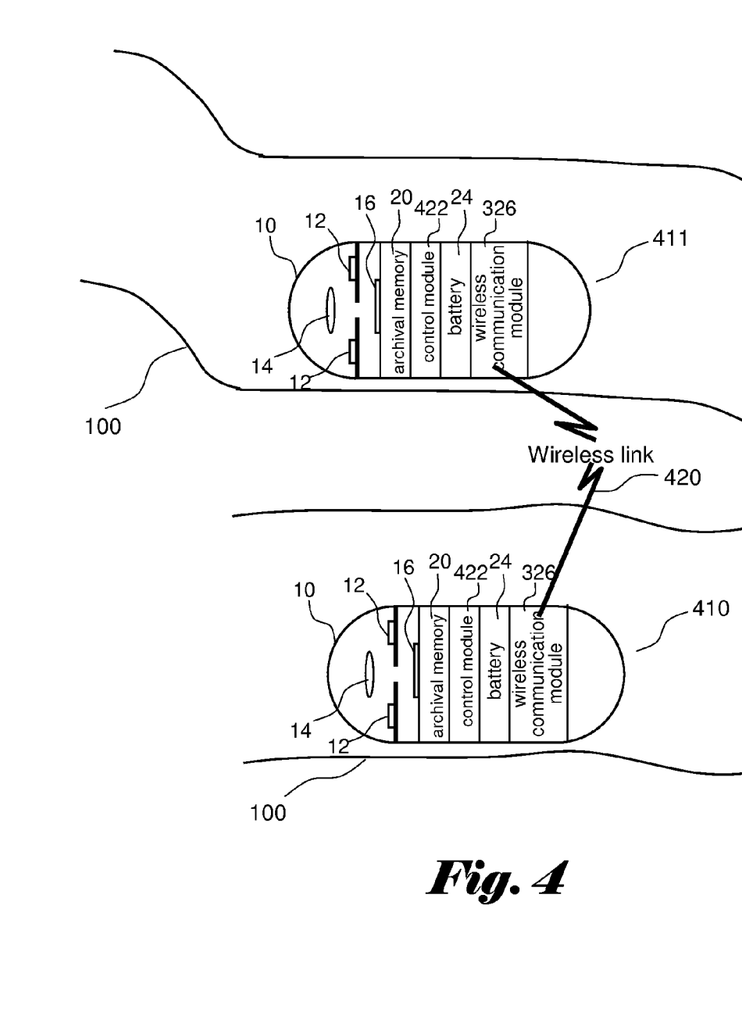
FIG. 4 shows schematically multiple capsule camera system, having a wireless communication module in each of the capsule camera, in the GI.

FIG. 4 shows an exemplary multiple capsule camera system, wherein two capsule cameras, a first capsule camera 410 and a second capsule camera 411, are used. While two capsule cameras are used in the exemplary multiple camera system, the multiple capsule camera system may use more than two capsule cameras. The first capsule camera 410 and the second capsule camera 411 may be swallowed at the same time or at different times. FIG. 4 illustrates a scenario that the two cameras are at two different sections inside the body lumen 100. Capsule cameras 410 and 411 include a respective control module 422. The wireless communication module 326 of the first capsule camera 410 and the wireless communication module 326 of the second capsule camera 411 form a wireless link to exchange information.

The two capsule cameras may communicate its status to each other in order to coordinate their operation modes accordingly. When a capsule camera is not in an active mode, it should stay in a power-saving sleep mode wherein the essential circuits are operational while other circuits may be turned off or in a mode consuming minimum power. The essential circuits may include a timer that keeps track of the time and alerts the system to activate other circuits when triggered by a pre-set time. For the capsule cameras 410 and 411, the essential circuits also include receiving circuits of the wireless communication module 326 so that the cameras 410 and 411 will be able to receive status information from the other wireless communication module in the sleep mode. In order to be able to process the data received from the wireless communication module 326, the processing unit such as a processor, a microcontroller, or a digital logic of the control module 326 should be awaked upon received data. The controller module then examines the received data from the wireless communication module 326 to determine the need for updating the operation mode of the respective camera.

In one example, the two capsule cameras are swallowed at substantially the same time and they will be likely located in close proximity with each other inside the body lumen 100. The first capsule camera 410 may enter the active mode first while the second camera 411 stays in the sleep mode initially. The first camera 410 transmits its battery status to the second camera 411 either on a periodic basis or on the event that the battery energy level becomes low. When the second camera 411 receives the battery status information from the first camera 410, it can make decision about its operation mode. For example, the control module may decide to let the second capsule camera 411 stay in the sleep mode if the battery energy level of the first capsule camera is still high, and to let the second capsule camera 411 to enter the active mode when the battery energy level of the first capsule camera 410 is lower than a pre-specified level. The two capsule cameras 410 and 411 can also be swallowed at different times separated by a period T. In this case, the second capsule camera 411 should be entered into the active mode at time T after the second capsule camera 411 receives low battery status from the first capsule camera 410. However, the second capsule camera 411 may be entered into the active mode earlier in order to add safe margin to accommodate the variations of traverse time between the two capsule cameras. In this example, the first capsule camera is deployed first and it only transmits its status information. Therefore, the wireless communication module of the first capsule camera may only have a wireless transmitter. On the other hand, the second capsule camera only receives status information from the first camera. Therefore, the wireless communication module of the second capsule camera may only have a wireless receiver.

The battery energy level is a measure to determine the remaining power in the battery. However, the measurement will require additional circuits. For example, the voltage level across the terminals of the battery can provide a good estimate of the remaining energy in the battery and the voltage can be measured with an analog to digital converter to obtain a numerical reading of the voltage level. A more precise battery energy level monitoring may involve the accumulation of current passing through a battery terminal Such measurement may further increase the system complexity and cost.

In order to simplify battery energy level measurement, an alternative approach based on the energy consumed by major energy consuming components is used to estimate the energy consumption. For example, the major energy consuming components in the capsule camera 410 and 411 are associated with the number of pictures captures by the image sensor and the illuminating time of the LED. The energy consumed for capturing each picture and the energy consumed by the illuminating LED in each time unit can be measured before hand. Therefore, by counting the number of pictures captured and the total time that the LED illuminates, the energy consumed by the battery can be estimated. The number of pictures captured can be tracked with the help of the processor, microcontroller or digital logic in the controller module, which is not shown in FIG. 4. The total time that the LED illuminates can also be tracked with the help of the processor, microcontroller or digital logic in the controller module, which is not shown in FIG. 4.

While the multiple camera system shown in FIG. 4 is a system that multiple capsule cameras coordinate among themselves without the assistance of an external device, the first capsule camera 410 and the second capsule camera 411 may require setting up the control module 326 differently. For example, the control codes of the control module for the first capsule camera 410 will be different from the control codes of the control module for the second capsule camera 411 in order to allow the first capsule camera 410 to enter the active mode ahead of the second capsule camera. Therefore two different types of capsule cameras have to be manufactured or programmed which may increase manufacturing cost and/or may complicate inventory management.

Figure 5:
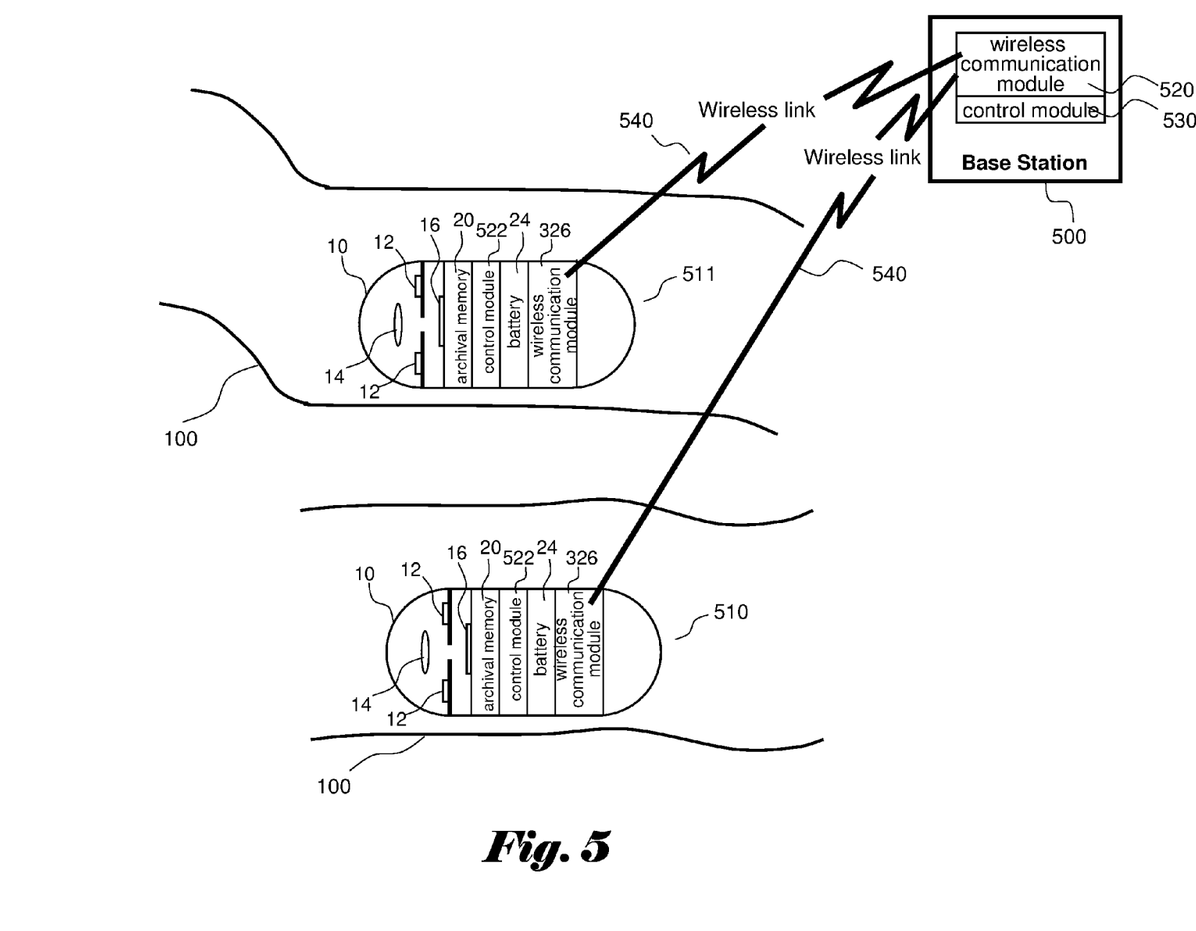
FIG. 5 shows schematically multiple capsule camera system, having a wireless communication module in each of the capsule camera, in the GI and with a base station having a wireless communication module.

FIG. 5 shows an alternative multiple capsule camera system wherein an external base station 500 is used. For the base station 500, only the components relevant to the present invention are shown which include a wireless communication module 520 and a control module 530. FIG. 5 shows an exemplary multiple capsule camera system, wherein two capsule cameras, a first capsule camera 510 and a second capsule camera 511, are used. While two capsule cameras are used in the exemplary multiple camera system, the multiple capsule camera system may use more than two capsule cameras. The first capsule camera 510 and the second capsule camera 511 may be swallowed at the same time or at different times. FIG. 5 illustrates a scenario that the two cameras are at two different sections inside the body lumen 100. Capsule cameras 510 and 511 include a respective control module 522. The wireless communication module 326 of the first capsule camera 510 can communicate with the base station 500 through wireless communication module 520. Similarly, the wireless communication module 326 of the second capsule camera 511 can communicate with the base station 500 through wireless communication module 520.

In one preferred embodiment of the present invention, each capsule camera will transmit its status information to the base station and receive instructions from the base station through the wireless link between wireless communication module 326 and wireless communication module 520. Under this arrangement, each capsule camera will be assigned an identification (ID) number and can be identified by the based station as part of the communication protocol through the wireless communication. The ID number can be stored in a memory device such as EEPROM, flash memory, or one-time/multiple-time programmable memory of the respective control module, which is not explicitly shown in the drawing. The ID can be programmed into the memory during manufacturing of the capsule camera and this process is fairly common for devices having the need for identifying the unit. The ID may also be programmed wirelessly or by other means at the clinics or other places of convenience. The base station 500 is outside the body and usually the power consumption and physical size are less concerned compared with the swallowable capsule camera. Therefore, the base station can be made with more processing capability to made more advanced decision. The base station may even be equipped with an antenna array to track the locations of the capsule cameras for more intelligent capsule camera coordination. Each capsule camera will transmit its status to the base station 500. The capsule camera status may include its battery status, the number of pictures it has imaged, and/or the electrical current of the illuminating LEDs.

The battery status is important information that the base station needs to know about the capsule cameras. It will help the base station to determine which capsule camera should be in the sleep mode and which capsule camera should be in the active mode and when. For example, the first capsule camera 510 and the second capsule camera 511 are approximately swallowed at the same time. The base station may instruct the first capsule camera to enter the active mode when the first capsule camera is expected to enter the section of the GI tract that it is intended to image. The base station 500 should keep the second capsule camera 511 in the sleep mode until the base station receives a low battery status from the first capsule camera 510. Since the capsule camera has to be able to listen to base station 500 for its instructions, the wireless communication module 326 of capsule camera should be able to receive signals in the sleep mode. Since the rate of movement of the capsule camera is not very reliable, the second capsule camera should be entered into an active mode earlier to accommodate the variations of its rate of movement. The capsule camera shown in FIG. 5 will have to transmit its status information and receive command from the based station, therefore, the wireless communication module will have both a wireless transmitter and a receiver that may be implemented as a combined transceiver. The wireless communication module for the based station will also have both a wireless transmitter and a receiver that may be implemented as a combined transceiver.

As mentioned earlier, important status information for the battery is its remaining energy level. The energy level can be estimated from the voltage level across the battery terminals and the voltage can be measured with an analog to digital converter to obtain a numerical reading of the voltage level. A more precise battery energy level monitoring may involve the accumulation of current passing through a battery terminal Such measurement may further increase the system complexity and cost.

A simplify battery energy level measurement was discussed previously. This method estimates the remaining battery energy level by estimating the energy consumed by the major energy consuming components in the capsule camera. For example, the major energy consuming components may be imaging sensor for capturing pictures and illuminating LEDs for illuminating. The energy consumed for capturing each picture and the power consumed by the illuminating LED in each time unit can be measured before hand. Therefore, by counting the number of pictures captured and the total time that the LED illuminates, the energy consumed by the battery can be estimated. The number of pictures captured can be tracked with the help of the processor, microcontroller or digital logic in the controller module, which is not shown in FIG. 5. The total time that the LED illuminates can also be tracked with the help of the processor, microcontroller or digital logic in the controller module, which is not shown in FIG. 5

The wireless communication between the capsule camera and base station for the coordination purpose is low power, low data rate and infrequent in order not to affect the operation time of the capsule camera. The amount of data transmitted between the capsule camera and the base station is relatively small due to the nature of the status information. The wireless communication does not have to be continuous because the battery status will not change abruptly. An interval of status transmission from several seconds to several minutes are reasonable without affecting the desired coordination. Alternatively, the status transmission can be polled by the base station which can poll less frequently during the early period of the camera operation and poll more frequent when the camera is anticipated to reach low battery status. As another alternative, the transmission of status information from the capsule camera can also be initiated by the capsule camera as triggered by a particular circumstance. For example, the capsule camera may monitor its battery voltage and transmit the status information to the base station only when the voltage falls below a pre-specified level. Other battery status information can be the electrical current level of the illuminating LEDs the number of pictures being imaged.

Figure 6:
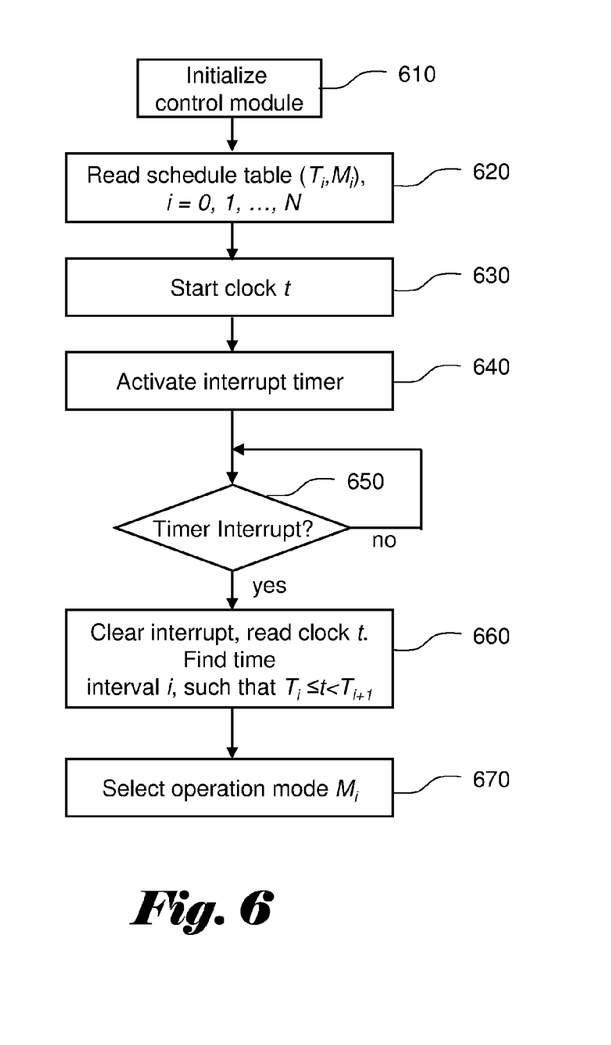
FIG. 6 shows the flow chart for the control module of the capsule camera system described in FIG. 2.

In the multiple capsule camera system, all the system coordination among capsule camera is controlled by the control module. FIG. 6 shows the flow chart for the control module in a multiple capsule camera system as shown in FIG. 2. This control module will go through initialization 610 upon the camera activation. In step 620, the control module will then read the schedule table from a memory. Now the control module is ready for its routine by starting the clock as shown in step 630. The control module then activate its interrupt time as shown in step 640 and wait for timer interrupt as shown in step 650. When a timer interrupt occurs, the control module will clear the interrupt, compare its current time against the time intervals of the schedule and determine the interval i that the current time falls in as shown in step 660. Upon the determination of the time interval, the control module will select the corresponding operation $M_i$ as shown in step 670. The flow chart is the same for the first capsule camera and the second capsule camera. The coordination is embedded in the respective schedule table to achieve the desired coordination. For capsule camera operation, usually there will be a period of time that the capsule camera stays in a sleep mode for a period of time initially. The flow chart shows the case that the initial delay in embedded into the schedule table. An alternative implementation may call for an explicit initial delay.

Figure 7:
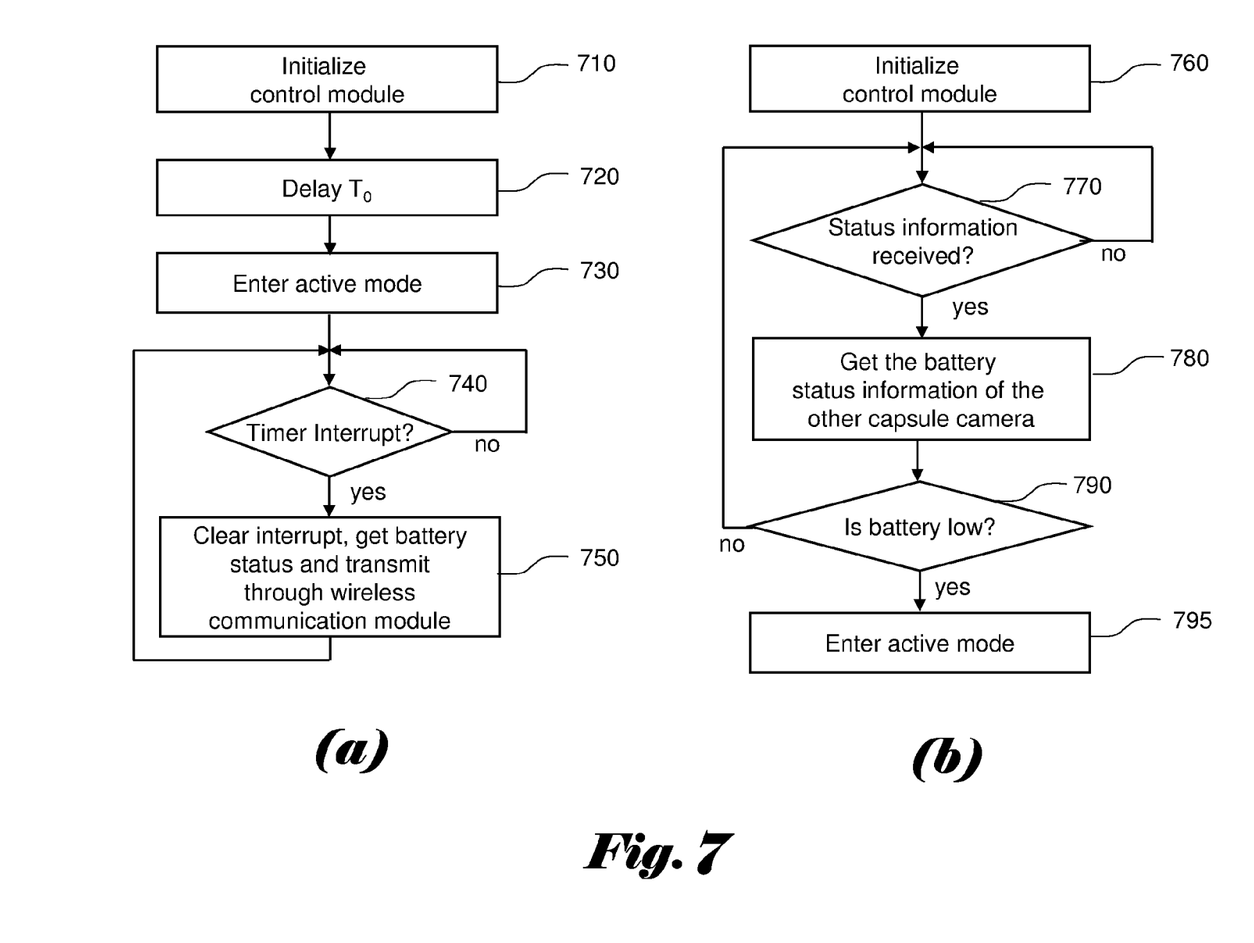
FIG. 7 shows the flow chart for the control module of the capsule camera system described in FIG. 4.

For the multiple capsule camera system shown in FIG. 4, the flow chart for the control modules will be different. FIG. 7a shows the flow chart for the control module of the first capsule camera and FIG. 7b shows the flow chart for the control module of the second capsule camera. For the control module of the first capsule camera, it will be initialized upon activation as shown in step 710. After waiting for an initial delay period as shown in step 720, it will be waken up to enter the active mode as shown in step 730, wherein its interrupt timer will be activated. The initial delay is added before entering the active mode in order to conserve capsule camera system energy if the camera is not going to image the upper GI tract. This step can be skipped if imaging is desired immediately after swallowed. The control module then waits for timer interrupt as shown in step 740. Upon triggering of timer interrupt, the control module will clear interrupt, read its battery status and transmit the status to the other control module as shown in step 750. The first capsule camera works as a master by informing the second capsule camera about its status. When its battery runs low, the other capsule camera should take over with some margin to accommodate variation of the rate of transverse inside the GI tract. Other alternatives can also achieve the goal. For example, the battery status will be transmitted only if the battery status indicates a low battery level.

FIG. 7b shows the flow chart for the control module of the second capsule camera. The second capsule camera works as a slave to pick up the imaging duty upon the notification of low battery level in the first capsule camera. The control module is initialized upon activation as shown in step 760. The control module then enters a sleep mode with the communication module in the receiving mode waiting for status information received from the communication module as shown in step 770. When status information is received from the communication module, the control module will get the battery status information of the other capsule camera as shown in step 780. The received battery status will be checked in step 790 to determine whether it reaches a low battery level. If so, the second camera will wake up and enter an active mode as shown in step 795.

Figure 8A:
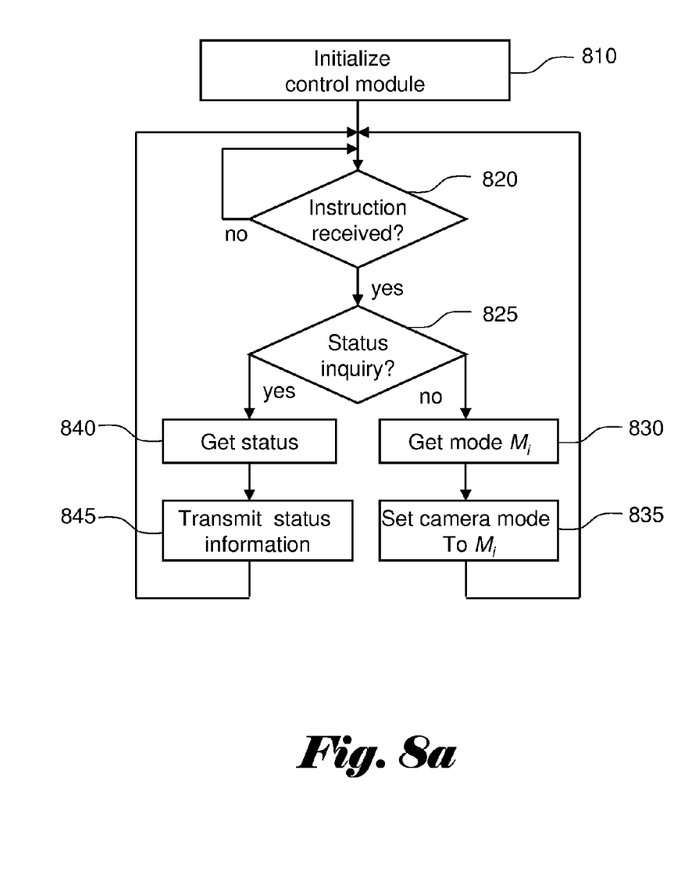
FIG. 8 shows the flow chart for the control module of the capsule camera system described in FIG. 5.

In the system using a base station as shown in FIG. 5, all the control modules inside the capsule camera will behave the same. The control module will listen to the instruction from the base station control module. FIG. 8a shows the flow chart for the control module at the capsule camera side. After the control module is initialized in step 810 and waits for initial delay in step 815, it will be in the loop to check whether an instruction is received from the base station control module as shown in step 820. When an instruction is received, it will check whether the instruction in a status inquiry or a new mode setting as shown in step 825. If it is a status inquiry, it will get the status as shown in step 840 and transmit as shown in step 845. After requested status information is transmitted, the control module goes back to wait for new instruction. If the received instruction is a new mode setting, it will get the mode as shown in step 830 and set the camera mode accordingly as shown in step 835. After the mode is set, the control module goes back to wait for new instruction.

Figure 8B:
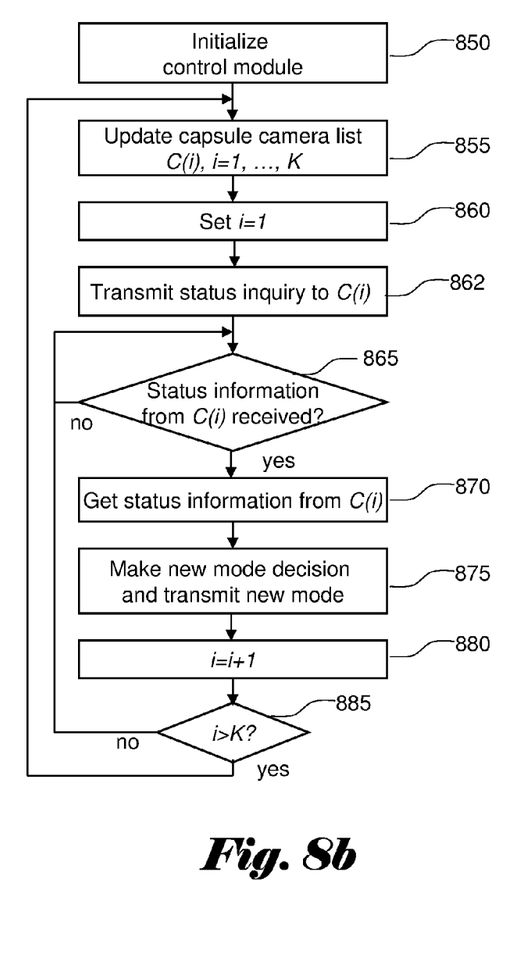

FIG. 8b shows a flow chart for the control module at the base station. After the control module is initialized in step 850, it will update the camera list as shown in step 855. Since some of the capsule cameras will run out battery, the control module does not need to manage those inactive cameras. The control module then send instruction to capsule cameras one by one by initializing the counter as shown in step 860 and send instruction to a corresponding capsule camera in step 862. After it sends the status inquiry, it will wait for reply from the corresponding camera control module as shown in step 865. Upon receiving status information, the control module will get the status information as shown in step 870 and determines the operation mode accordingly as shown in step 875. The control module then moves on to the next camera by incrementing the counter as shown in step 880. It will then check whether the last camera is reached as shown in step 885. If it is not the last camera, it will continue to inquire the status for the next camera. If it reaches the last camera, it will update its camera list and go through all cameras for status inquiry and determine new mode again.

The above detailed description illustrates the specific embodiments of the present invention and is not intended to be limiting. Numerous modifications and variations within the scope of the invention are possible. The present invention is set forth in the following claims.

The invention claimed is:

1. A cooperative multiple capsule camera apparatus, comprising:
   a first capsule cameras, wherein the first capsule camera includes a first battery, a first image sensor, first LEDs, a wireless transmitter and a first control module;
   a second capsule cameras, wherein the second capsule camera includes a second battery, a second image sensor, second LEDs, a wireless receiver and a second control module; and
   a base station having a wireless communication module and a third control module;
   wherein the first control module provides first information to the third control module through a first wireless link from the wireless transmitter to the wireless communication module;
   wherein the second control module receives second information from the third control module through a second wireless link from the wireless communication module to the wireless receiver; and
   wherein the first information transmitted from the wireless transmitter to the wireless communication module includes status information of the first capsule camera and the status information includes battery status, a number of pictures captured by the first image sensor, or a total time period of illumination of the first LEDs.

2. The apparatus of claim 1, wherein the second capsule camera enters an active mode from a sleep mode as indicated in the second information.

3. The apparatus of claim 2, wherein transmitting status information from the first control module to the base station is triggered by low battery status, energy consumption profile, a low electrical current value of the first LEDs, or a number of pictures captured by the image sensor, or a combination thereof.

4. The apparatus of claim 1, wherein the third control module generates the second information according to the first information.

5. A method of operating a cooperative multiple capsule camera, the method comprising:

providing a first capsule cameras, wherein the first capsule camera includes a first battery, a first image sensor, first LEDs, a wireless transmitter and a first control module;

providing a second capsule cameras, wherein the second capsule camera includes a second battery, a second image sensor, second LEDs, a wireless receiver and a second control module; and providing a base station having a wireless communication module and a third control module;

wherein the first control module provides first information to the third control module through a first wireless link from the wireless transmitter to the wireless communication module;

wherein the second control module receives second information from the third control module through a second wireless link from the wireless communication module to the wireless receiver; and wherein the first information transmitted from the wireless transmitter to the wireless communication module includes status information of the first capsule camera and the status information includes battery status, a number of pictures captured by the first image sensor, or a total time period of illumination of the first LEDs.

6. The method of claim 5, wherein the second capsule camera enters an active mode from a sleep mode as indicated in the second information.

7. The method of claim 6, wherein transmitting status information from the first control module to the base station is triggered by low battery status, energy consumption profile, a low electrical current value of the first LEDs, or a number of pictures captured by the image sensor, or a combination thereof.

8. The method of claim 5, wherein the third control module generates the second information according to the first information.

* * * * *